United States Patent
Feldman et al.

(10) Patent No.: US 8,095,385 B2
(45) Date of Patent: Jan. 10, 2012

(54) METHOD AND SYSTEM TO TRACK CUSTOMER PURCHASES

(75) Inventors: Jay Feldman, Richboro, PA (US); Michael Wieczkowski, Hamilton, NJ (US)

(73) Assignee: IMS Software Services Ltd., Plymouth Meeting, PA (US)

( * ) Notice: Subject to any disclaimer, the term of this patent is extended or adjusted under 35 U.S.C. 154(b) by 1493 days.

(21) Appl. No.: 10/505,646

(22) PCT Filed: Feb. 21, 2003

(86) PCT No.: PCT/US03/05231
§ 371 (c)(1),
(2), (4) Date: Sep. 8, 2005

(87) PCT Pub. No.: WO03/073346
PCT Pub. Date: Sep. 4, 2003

(65) Prior Publication Data
US 2006/0074717 A1 Apr. 6, 2006

Related U.S. Application Data

(60) Provisional application No. 60/358,866, filed on Feb. 21, 2002.

(51) Int. Cl.
*G06F 19/00* (2011.01)

(52) U.S. Cl. ................................. 705/3; 705/2
(58) Field of Classification Search ............... 707/102; 705/2, 3, 37, 26, 21; 600/300
See application file for complete search history.

(56) References Cited

U.S. PATENT DOCUMENTS

| | | | |
|---|---|---|---|
| 5,519,607 A | 5/1996 | Tawil | 364/401 |
| 5,666,492 A | 9/1997 | Rhodes et al. | 705/3 |
| 5,737,539 A | 4/1998 | Edelson et al. | 395/203 |
| 5,758,095 A | 5/1998 | Albaum et al. | 395/202 |
| 5,911,132 A * | 6/1999 | Sloane | 705/3 |
| 6,397,224 B1 * | 5/2002 | Zubeldia et al. | 707/102 |
| 7,630,908 B1 * | 12/2009 | Amrien et al. | 705/3 |
| 2002/0065758 A1 * | 5/2002 | Henley | 705/37 |
| 2002/0091576 A1 * | 7/2002 | Giordano et al. | 705/26 |
| 2002/0165736 A1 | 11/2002 | Tolle et al. | |
| 2004/0019502 A1 * | 1/2004 | Leaman et al. | 705/2 |
| 2005/0060197 A1 * | 3/2005 | Mayaud | 705/2 |
| 2005/0119941 A1 * | 6/2005 | James | 705/26 |

* cited by examiner

*Primary Examiner* — Gerald J. O'Connor
*Assistant Examiner* — Natalie A Pass
(74) *Attorney, Agent, or Firm* — Baker Botts LLP

(57) ABSTRACT

A system and method for identifying transactions relating to a single customer in a data set received from a plurality of outlets (402), such that one patient's (404) pharmaceutical prescription data may be linked (406) to represent the entire pharmaceutical purchases of said patient is disclosed (414).

17 Claims, 5 Drawing Sheets

```
┌─────────────────────────┐
│ OUTLET #                │ ←── 102
│ OUTLET PATIENT ID       │
│ Rx #                    │
│ TRANSACTION DATE        │
│ Dr. #                   │
└─────────────────────────┘
            ·
            ·
            ·
            ·
            n
```

FIG. 2

```
┌─────────────────────────┐
│ PBM PATIENT ID          │ ←── 112
│ Rx #                    │
│ OUTLET #                │
│ TRANSACTION DATE        │
│ Dr. #                   │
└─────────────────────────┘
            ·
            ·
            ·
            ·
            n
```

FIG. 3

| PBM ID | Rx # | OUTLET # | TRANSACTION DATE | Dr. # |
|---|---|---|---|---|
| 1023 | H2WXY | 102 | 1/31/02 | Z46 |
| 1023 | H2WAB | 104 | 1/5/02 | Z46 |

| OUTLET PATIENT ID | Rx # | OUTLET # | TRANSACTION DATE | Dr. # |
|---|---|---|---|---|
| 7102 | H2WXY | 102 | 1/31/02 | Z46 |
| 522 | H6WAB | 104 | 1/5/02 | Z46 |
| 7102 | H8XWZ | 102 | 1/10/02 | Z46 |

FIG. 5

| OUTLET PATIENT ID | INTERNAL ID | PBM ID |
|---|---|---|
| 7102 | 4001 | |
| 522 | 4002 | |
| | | |
| | | |

FIG. 6(a)

| OUTLET PATIENT ID | INTERNAL ID | PBM ID |
|---|---|---|
| 7102 | 4001 | 1023 |
| 522 | 4002 | 1023 |
| | | |
| | | |

FIG. 6(b)

METHOD AND SYSTEM TO TRACK CUSTOMER PURCHASES

CROSS-REFERENCE TO RELATED APPLICATION

This application is related to U.S. Provisional Patent Application 60/358,866, filed on Feb. 21, 2002, from which priority is claimed.

FIELD OF THE INVENTION

The present invention is directed to techniques for identifying transactions relating to a single individual customer in a data set of compiled prescription data, relating to pharmaceutical prescription (sales) transactions, from a plurality of data sources.

BACKGROUND INFORMATION

The pharmaceutical industry is one of the largest income generating industries in the world. As revenue in this industry has steadily increased, it has become increasingly important to track the prescribing habits of individual physicians.

Currently, pharmaceutical outlets ("outlets") record and store data pertaining to each pharmaceutical purchase by patients at such outlets. Outlets are more commonly known as drugstores or pharmacies. When a patient purchases pharmaceuticals from an outlet, the outlet collects data such as the patient's name, the pharmaceutical item dispensed ("Rx #"), the transaction date, the physician who prescribed the prescription ("Dr. #"), and other miscellaneous information.

As this transaction information is recorded in the outlet's database, the outlet typically assigns each patient an identification code ("outlet identifier"). An outlet identifier is used such that a patient's name can remain anonymous when such information is transmitted outside of the outlet. Since each outlet may be a drugstore, pharmacy, or chain thereof, outlet identifiers are not the same across multiple outlets. Further, where an outlet is a chain of drugstores, an outlet identifier may not even be the same across different stores of that same chain.

For example, if one outlet is pharmacy "ABC", a regular consumer/patient John Doe may have an outlet identifier "00A" at pharmacy ABC. If John Doe then gets a pharmaceutical filled from drugstore XYZ, John Doe will general get a different outlet identifier, "001" for example, at pharmacy XYZ. Thus, even though John Doe is only one individual patient, if prescription data from both pharmacies are received by a central source, John Doe's records appear as that of two different patients because of the unlike identifiers across different outlets. Thus, based upon the currently available data it is very difficult to map and/or track the pharmaceutical prescriptions written for John Doe or by Joe Doe's physician because John Doe's records appear as two (2) different patients across multiple outlets.

Pharmaceutical benefit managers ("PBM") are another group in the pharmaceutical industry that collect data. In particular, PBMs collect data that pertain to pharmaceutical sales that get resolved through insurance plans. For example, if a patient John Doe has a particular health insurance, "MNO" health insurance, and John Doe wishes to use his benefits under MNO to pay for all or part of his pharmaceutical purchase, data will then pass from the dispensing outlet to one or more PBMs of such transaction, as the transaction is cleared with the insurance company.

PBM data is similar to the outlet prescription data described above. PBM data typically includes an outlet identifier, Rx #, the transaction date, Dr. #, other miscellaneous information, and a patient identifier given by the pharmaceutical benefit manager. Although the pharmaceutical benefit manager can identify patients across a plurality of outlets, because patients are identified by a health insurance plan and an unique identifier for that health insurance (not outlet identifiers as described above), a PBM cannot track cash transactions, or transactions related to insurance plans not serviced by that PBM. Thus, the PBM also cannot provide an accurate depiction of a physician's dispensing habits.

What is needed is an efficient and effective way to track a patient's pharmaceutical prescriptions (sales) across a period of time and across outlets where all prescription information related to a unique patient can be linked regardless of the data source for the information.

SUMMARY OF THE INVENTION

An object of the present invention is to provide a technique for identifying transactions pertaining to an individual in a data set of compiled patient pharmaceutical prescription data from a plurality of outlets, so that one patient's pharmaceutical prescription data may be linked across time to represent the entire pharmaceutical purchases of the patient so as to track the prescribing doctor's prescribing habits.

In order to achieve this objective, as well as others which will become apparent in the disclosure below, the present invention provides techniques for receiving patient pharmaceutical prescription data ("prescription data") from a plurality of outlets and from one or more PBMs, and linking prescription data records ("record") pertaining to an individual across data sources to provide a clear view of a patient's pharmaceutical purchases and physician prescribing patterns.

In a preferred embodiment, prescription data is received from a plurality of data sources. Such prescription data contains patient identifiers marked by its originating data source in accordance with that data source's own identification scheme. All records are stored in a general storage area. In addition, each unique patient identifier is also stored in a data relation table. Further, each unique patient identifier in the table is assigned an internal identifier.

Next, as will be further described below, all records in the storage area are checked by a triangulation engine which, by keying in on the Rx #, outlet number, transaction date, and Dr. #, compares records in the storage area with reference data received from one or more PBMs for similarities. In particular, if the above attributes of a prescription sales record in the storage area match a record of reference data from a PBM, the table is updated such that the patient identifier, for the matched record, is associated with a matched PBM identifier to reflect a bridge between the patient identifier of the record and the associated PBM identifier.

In a preferred embodiment, the table is then checked to ensure that each unique PBM identifier is cross-referenced to only one internal identifier in the table, and updates the table accordingly. Thus, by querying on the internal identifier, a patient's pharmaceutical history can be tracked by keying in on only one identifier, regardless of the origins of such data.

Advantageously, the data in the storage area is then made available for tracking prescriptions relating to a unique individual across the value chain. This linking methodology allows for better prescription analysis by providing the ability to link prescription data longitudinally across data sources.

BRIEF DESCRIPTION OF THE DRAWINGS

For a complete understanding of the present invention and the advantages thereof, reference is now made to the following description taken in conjunction with the accompanying drawings in which like reference numbers indicate like features, components and method steps, and wherein:

FIG. 2 is an illustrative diagram of exemplary fields in each record of information transmitted from the outlets to the system of the present invention;

FIG. 3 is an illustrative diagram of exemplary fields transmitted from the pharmacy benefit managers to the system of the present system;

FIG. 5 is a chart illustrating an example of the cross-referencing of records performed by the present invention;

FIG. 6(a) is a representative illustration of a table of the present invention before bridging is performed by the triangulation engine; and FIG. 6(b) is a representative illustration of a table of the present invention after bridging is performed by the triangulation engine.

DESCRIPTION OF A PRESENTLY PREFERRED EMBODIMENT

Figure 1:
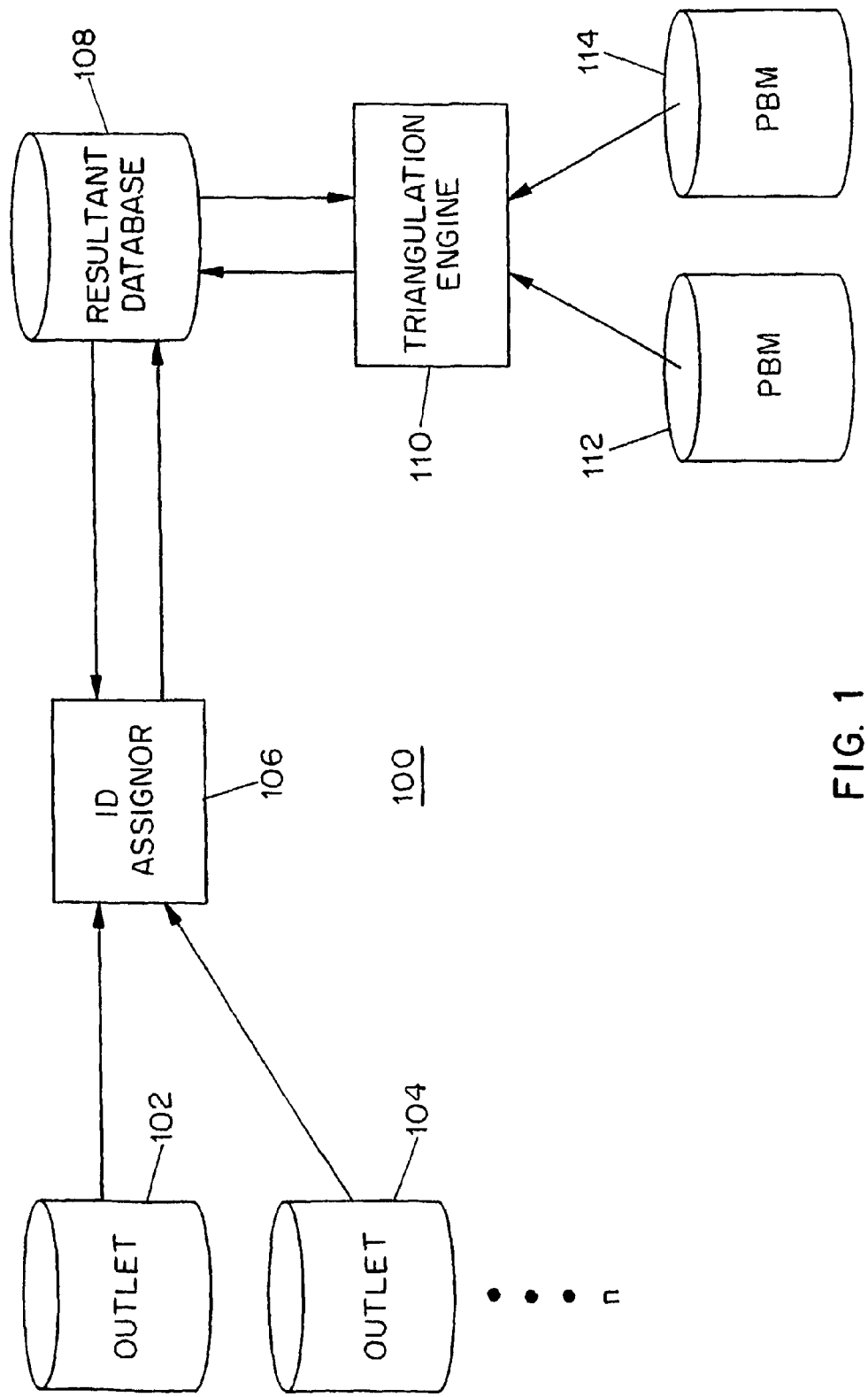
FIG. 1 is a functional diagram of an exemplary system of the present invention.

Referring to FIG. 1, in a preferred embodiment the present system 100 includes a plurality of outlets 102, 104 which are coupled to an identification assignor ("ID assignor") 106. The ID assignor 106 is in turn coupled to a resultant database 108. The present system 100 also includes one or more PBMs 112, 114. PBMs 112, 114 are coupled to triangulation engine 110. Triangulation engine 110 is coupled to the database 108 such to exchange and receive data therewith.

The triangular engine 110 and ID assignor 106 may be personal computers, networked computers or computer servers, or mainframe devices. Similarly, database 108 may be a relational database, where links and relations can be formed between uncommon fields across multiple records, such as Oracle(TM) or Sybase(TM), residing on a hard drive or magneto-optical device on a personal computer, networked computer or computer server, or mainframe device. ID assignor 106, triangulation engine 110, and database 108 may communicate and exchange data on a plurality of computer networks known in the art, including operating under protocols such as the Transmission Control Protocol/Internet Protocol ("TCP/IP").

Referring next to FIG. 2, using outlet 102 as a representative example of outlets, outlet 102 transmits prescription data records to ID assignor 106 pertaining to pharmaceutical prescriptions (sales) to patients from outlet 102. The records may contain a variety of fields, preferably, the outlet number, outlet patient ID, Rx #, the transaction date, and Dr. # (which is the prescribing physician as described above). Preferably all outlets sending records to ID assignor 106 have records in similar formats.

Referring to FIG. 3, FIG. 3 shows exemplary fields transmitted by one or more PBMs to the triangular engine 110. Each record a PBM transmits to the triangulation engine preferably includes the PBM patient ID number, Rx #, outlet number, transaction date, and Dr. #.

Figure 4:
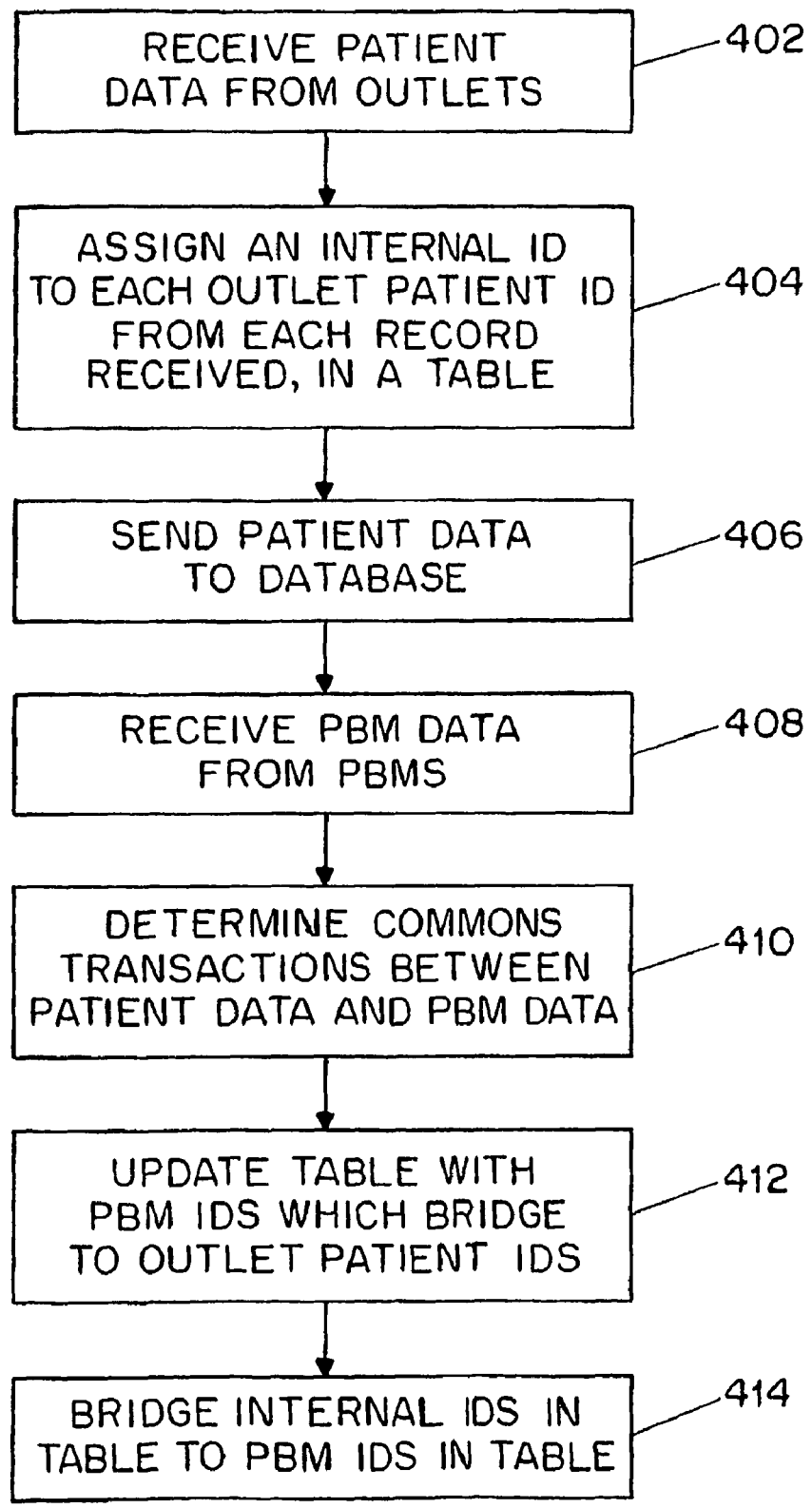
FIG. 4 is a flow diagram showing the basic process flow for identifying transactions related to a single customer in data set received from multiple outlets in accordance with the present invention.

Referring to FIG. 4, in an exemplary embodiment, in operation ID assignor 106 receives records from outlets 102, 104 in step 402. Since different outlets, or chains of outlets, use different patient identifier schemes, once ID assignor 106 receives records from outlets 102, 104, ID assignor 106 places each unique outlet patient ID in a table residing in database 108, and assigns each outlet patient ID in the table with an internal ID in step 404. In this way all outlet patient IDs held have a common patient identification scheme once received by the present system. ID assignor 106 may comprise a network computer server, personal computer, or mainframe, for example, for receiving the records from the outlets 102, 104.

After ID assignor 106 assigns an internal ID to each unique outlet patient ID in the table in database 108, ID assignor 106 then updates a records storage area of database 108 with the new records received in step 402, in step 406.

Next, triangulation engine 110 receives PBM data from one or more PBMs 112, 114 in step 408. Once received, the triangulation engine 110 takes the PBM data received, and queries the records storage area of database 108 record-by-record trying to cross-reference the fields in the PBM data with records in the records storage area of database 108 to determine prescription transactions which are the same, in step 410. Based upon such determination, the triangulation engine 110 then updates the table in database 108 to reflect where an outlet patient ID maps to a PBM ID, in step 412. Lastly, the triangulation engine maps each unique PBM ID to only one internal ID to be used in subsequent queries, in step 414. Similar to ID assignor 106, the triangulation engine 110 may comprise a network computer server, personal computer, or mainframe, for example, for receiving the PBM data.

Referring to FIG. 5 as an illustrative example, triangular engine 110 may receive PBM data 502, 504. The records storage area of database 108 may contain the three (3) records illustrated in data set 506 received from outlet records passed through ID assignor 106. The three transactions are in actuality from one patient, where such patient filled "H2WXY" at outlet 102 using his health insurance plan, filled "H6WAB" at outlet 104 using his health insurance plan, and filled "H8XWZ" at outlet 102 paying for the prescription in cash.

Taking these records for purposes of this illustrative example, prior to being passed to the records storage area of database 108, the ID assignor 106 populated the table in database 106 with the outlet patient IDs in 506, and assigned internal IDs for each, as illustrated in FIG. 6(a). As analyzed by the triangulation engine 110, the first transaction with outlet patient ID 7102 is linked to PBM data 502 with a PBM ID of "1023," because, as is clear, all other fields match. Similarly, the second transaction with outlet patient ID 522 is linked to PBM data 504 also with PBM ID "1023". Since the third transaction is also for outlet patient ID 7102, it is also linked to PBM ID "1023".

These values are updated and stored in the table in database 108, and upon updating the table with the PBM IDs, the triangulation engine 110 ensures that each unique PBM ID has only one corresponding internal ID. This is illustrated in FIG. 6(b), which is the table, in this example, after linking. In this way, by querying on the internal ID, all of one patient prescription transacitons will be revealed.

The above system and method may be implemented by many computer languages commonly known in the art and may operate on many computer platforms which include both volatile and non-volatile memory storage devices. In a preferred embodiment, the system and method of the present invention is implemented, in whole or in part, on a mainframe, or UNIX based system using Oracle, SQL, and SAS. Software code encapsulating the functionality of the present inventive technique may be implemented on such computer systems, preferably written in Oracle PL*SQL, C, C++, or any other commonly known programming language.

Although the invention has been described herein by reference to an exemplary embodiment thereof, it will be understood that such embodiment is susceptible of modification and variation without departing from the inventive concepts disclosed. For example, the prescription data records received from the outlets could be used as the reference data and the information received from the PBMs could be the data which resides in database 108 for augmentation by the triangulation engine 110. Further, other types of data and other data formats than that represented in FIGS. 2 and 3 may be utilized in the present system and method. All such modifications and variations, therefore, are intended to be encompassed within the spirit and scope of the appended claims.

The invention claimed is:

1. A system for identifying sales transactions related to a single customer in a data set received from multiple pharmaceutical outlets, comprising:

one or more inputs for receiving patient pharmaceutical prescription information from a plurality of pharmaceutical outlets, said patient pharmaceutical prescription information including information identifying one or more patients and a unique outlet patient identifier for each of said pharmaceutical prescription patients, and for receiving pharmaceutical benefit manager information from one or more pharmaceutical benefit managers, said pharmaceutical benefit manager information including information identifying one or more pharmaceutical benefit manager patients and a unique pharmaceutical benefit manager identifier for each of said pharmaceutical benefit manager patients, said information identifying one or more patients comprising pharmaceutical prescription sales transaction information for said pharmaceutical prescription patients and said information identifying one or more pharmaceutical benefit manager patients comprising pharmaceutical prescription sales transaction information for said pharmaceutical benefit manager patients;

an identification assignor, coupled to said one or more inputs and receiving said patient pharmaceutical prescription information therefrom, for providing an internal patient identifier for each of said outlet patient identifiers in said patient pharmaceutical prescription information;

a triangulation engine, coupled to said one or more inputs for receiving said pharmaceutical benefit manager information and said patient pharmaceutical prescription information therefrom, for comparing said pharmaceutical benefit manager information to said patient pharmaceutical prescription information, wherein said comparing comprises matching said pharmaceutical prescription sales transaction information for said pharmaceutical prescription patients with said pharmaceutical prescription sales transaction information for said pharmaceutical benefit manager patients, and for; and a storage device, coupled to said identification assignor and receiving said patient pharmaceutical prescription information, said outlet patient identifiers and associated internal patient identifiers therefrom, and coupled to a triangulation engine for receiving pharmaceutical benefit manager identifiers therefrom, and maintaining a table for linking said outlet patient identifiers, said internal identifiers and said pharmaceutical benefit manager identifiers;

wherein said triangulation engine further analyzes said records in said table to ensure that each unique pharmaceutical benefit manager identifier is linked to only one internal identifier and modifying said records such that each unique pharmaceutical benefit manager identifier is linked to only one internal identifier.

2. The system of claim 1, further comprising a second storage device, coupled to said triangulation engine, for storing said table.

3. The system of claim 1, where said storage device comprises a hard disk drive.

4. The system of claim 1, where said storage device comprises a magneto-optical disc.

5. The system of claim 1, where said storage device comprises a relational database.

6. The system of claim 1, where said one or more inputs comprise a network computer server.

7. The system of claim 1, where said one or more inputs comprise a personal computer.

8. The system of claim 1, where said one or more inputs comprise a mainframe computer.

9. A method for identifying sales transactions related to a single customer in a data set received from multiple pharmaceutical outlets, comprising the steps of:

receiving patient pharmaceutical prescription information from a plurality of pharmaceutical outlets, said patient pharmaceutical prescription information including information identifying one or more patients and a unique outlet patient identifier for each of said pharmaceutical prescription patients, said information identifying one or more patients comprising pharmaceutical prescription sales transaction information for said pharmaceutical prescription patients;

receiving pharmaceutical benefit manager information from one or more pharmaceutical benefit managers, said pharmaceutical benefit manager information including information identifying one or more pharmaceutical benefit manager patients and a unique pharmaceutical benefit manager identifier for each of said pharmaceutical benefit manager patients, said information identifying one or more pharmaceutical benefit manager patients comprising pharmaceutical prescription sales transaction information for said pharmaceutical benefit manager patients;

assigning an internal patient identifier for each of said outlet patient identifiers in said received patient pharmaceutical prescription information;

storing said internal patient identifier and associated outlet patient identifier in a table, said table comprising one record for each associated internal patient identifier and outlet patient identifier pair;

storing said pharmaceutical prescription information in a storage area;

comparing, by a computer processor, said patient pharmaceutical prescription information with said pharmaceutical benefit manager information to determine matches in sales transactions, to define links between said outlet patient identifiers and said pharmaceutical benefit manager identifiers, wherein said comparing comprises matching said pharmaceutical prescription transaction information for said pharmaceutical prescription patients with said pharmaceutical prescription transaction information for said pharmaceutical benefit manager patients;

updating said table to reflect links between said outlet patient identifiers and said pharmaceutical benefit manager identifiers; and analyzing said records in said table to ensure that each unique pharmaceutical benefit manager identifier is linked to only one internal identifier and modifying said records such that each unique pharmaceutical benefit manager identifier is linked to only one internal identifier.

10. The method of claim 9, wherein said step of receiving patient pharmaceutical prescription information from a plurality of pharmaceutical outlets comprises receiving said patient pharmaceutical prescription information over a computer network.

11. The method of claim 9, where said step of receiving pharmaceutical benefit manager information from one or more pharmaceutical benefit managers comprises receiving said pharmaceutical benefit manager information over a computer network.

12. The method of claim 9, wherein said pharmaceutical prescription sales transaction information for said pharmaceutical prescription patients comprises an Rx #, outlet number, transaction date, and Dr. #.

13. The method of claim 12, wherein said pharmaceutical prescription sales transaction information for said pharmaceutical benefit manager patients comprises an Rx #, outlet number, transaction date, and Dr. #.

14. The method of claim 13, wherein said comparing comprises matching said Rx #, outlet number, transaction date, and Dr. # of said pharmaceutical prescription sales transaction information for said pharmaceutical prescription patients with said Rx #, outlet number, transaction date, and Dr. # of said pharmaceutical prescription sales transaction information for said pharmaceutical benefit manager patients.

15. The method of claim 9, wherein said pharmaceutical prescription sales transaction information for said pharmaceutical prescription patients comprises an Rx #, outlet number, transaction date, and Dr. #.

16. The method of claim 15, wherein said pharmaceutical prescription sales transaction information for said pharmaceutical benefit manager patients comprises an Rx #, outlet number, transaction date, and Dr. #.

17. The method of claim 16, wherein said comparing comprises matching said Rx #, outlet number, transaction date, and Dr. # of said pharmaceutical prescription sales transaction information for said pharmaceutical prescription patients with said Rx #, outlet number, transaction date, and Dr. # of said pharmaceutical prescription sales transaction information for said pharmaceutical benefit manager patients.

* * * * *